(12) United States Patent
Macneil et al.

(10) Patent No.: US 10,070,795 B2
(45) Date of Patent: *Sep. 11, 2018

(54) SYSTEM AND METHOD TO DEFINE A ROTATIONAL SOURCE ASSOCIATED WITH A BIOLOGICAL RHYTHM DISORDER

(71) Applicant: Topera, Inc., Menlo Park, CA (US)

(72) Inventors: William Robert Macneil, Oakville, MO (US); Ruchir Sehra, Scottsdale, AZ (US)

(73) Assignee: Topera, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/216,092

(22) Filed: Jul. 21, 2016

(65) Prior Publication Data

US 2016/0324430 A1 Nov. 10, 2016

Related U.S. Application Data

(63) Continuation of application No. 14/220,662, filed on Mar. 20, 2014, now Pat. No. 9,398,860, which is a
(Continued)

(51) Int. Cl.
*A61B 5/04* (2006.01)
*A61B 5/024* (2006.01)
(Continued)

(52) U.S. Cl.
CPC ........ *A61B 5/02405* (2013.01); *A61B 5/0245* (2013.01); *A61B 5/044* (2013.01);
(Continued)

(58) Field of Classification Search
CPC ......... A61B 5/02; A61B 5/04; A61B 5/04011; A61B 5/0402
See application file for complete search history.

(56) References Cited

U.S. PATENT DOCUMENTS

| 5,121,750 A | 6/1992 | Katims |
| 5,172,699 A | 12/1992 | Svenson et al. |

(Continued)

FOREIGN PATENT DOCUMENTS

| CN | 101939044 A | 1/2011 |
| CN | 102150072 A | 8/2011 |

(Continued)

OTHER PUBLICATIONS

Saksena, Sanjeev, et al "Electrophysiology and Endocardial Mapping of Induced Atrial Fibrillation in Patients with Spontaneous Atrial Fibrillation", American Journal of Cardiology, vol. 83, 1999, pp. 187-193.

(Continued)

*Primary Examiner* — Eric D. Bertram
(74) *Attorney, Agent, or Firm* — Hoffmann & Baron, LLP

(57) ABSTRACT

An example system and method of defining a rotational source associated with a heart rhythm disorder are disclosed. A plurality of center locations of wave fronts are calculated at a plurality of time points associated with the heart rhythm disorder. A rotational path that connects the plurality of center locations is then determined. Thereafter, a clinical representation that identifies a region of heart tissue associated with the rotational path is generated. The system and method can also determine a likely core associated with the rotational path. A plurality of relative diffusion shapes associated with the plurality of the center locations is calculated. A plurality of intersecting points of a smallest relative diffusion shape and other relative diffusion shapes is determined within the rotational path. A bounded polygon of the intersecting points is defined as the likely core.

24 Claims, 7 Drawing Sheets

Related U.S. Application Data continuation of application No. 13/840,354, filed on Mar. 15, 2013, now Pat. No. 8,715,199.

(51) Int. Cl.

| | | |
|---|---|---|
| *A61B 5/0245* | (2006.01) | |
| *A61B 5/0452* | (2006.01) | |
| *A61B 5/044* | (2006.01) | |
| *G06K 9/46* | (2006.01) | |
| *A61B 5/042* | (2006.01) | |
| *G06T 7/12* | (2017.01) | |

(52) U.S. Cl.
CPC ...... *A61B 5/04011* (2013.01); *A61B 5/04012* (2013.01); *A61B 5/0422* (2013.01); *A61B 5/0452* (2013.01); *G06K 9/4604* (2013.01); *G06T 7/12* (2017.01); *A61B 2576/023* (2013.01); *G06T 2207/30048* (2013.01)

(56) References Cited

U.S. PATENT DOCUMENTS

| | | | |
|---|---|---|---|
| 5,427,112 A | 6/1995 | Noren et al. | |
| 5,433,198 A | 7/1995 | Desai | |
| 5,450,846 A | 9/1995 | Goldreyer | |
| 5,480,422 A | 1/1996 | Ben-Haim | |
| 5,487,391 A | 1/1996 | Panescu | |
| 5,582,173 A | 12/1996 | Li | |
| 5,657,755 A | 8/1997 | Desai | |
| 5,662,108 A | 9/1997 | Budd et al. | |
| 5,718,241 A | 2/1998 | Ben-Haim et al. | |
| 5,795,303 A | 8/1998 | Swanson et al. | |
| 5,817,134 A | 10/1998 | Greenhut et al. | |
| 5,840,025 A | 11/1998 | Ben-Haim | |
| 5,848,972 A | 12/1998 | Triedman et al. | |
| 5,868,680 A | 2/1999 | Steiner et al. | |
| 5,954,665 A | 9/1999 | Ben-Haim | |
| 6,052,618 A | 4/2000 | Dahlke et al. | |
| 6,066,094 A | 5/2000 | Ben-Haim | |
| 6,188,924 B1 | 2/2001 | Swanson et al. | |
| 6,236,883 B1 | 5/2001 | Ciaccio et al. | |
| 6,256,540 B1 | 7/2001 | Panescu et al. | |
| 6,301,496 B1 | 10/2001 | Reisfeld | |
| 6,360,121 B1 | 3/2002 | Shoda | |
| 6,522,905 B2 | 2/2003 | Desai | |
| 6,584,345 B2 | 6/2003 | Govari | |
| 6,847,839 B2 | 1/2005 | Ciaccio et al. | |
| 6,856,830 B2 | 2/2005 | He | |
| 6,892,091 B1 | 5/2005 | Ben-Haim et al. | |
| 6,920,350 B2 | 7/2005 | Xue et al. | |
| 6,941,166 B2 | 9/2005 | MacAdam et al. | |
| 6,959,212 B2 | 10/2005 | Hsu et al. | |
| 6,975,900 B2 | 12/2005 | Rudy et al. | |
| 6,978,168 B2 | 12/2005 | Beatty et al. | |
| 7,016,719 B2 | 3/2006 | Rudy et al. | |
| 7,043,292 B2 | 5/2006 | Tarjan et al. | |
| 7,117,030 B2 | 10/2006 | Berenfeld et al. | |
| 7,123,954 B2 | 10/2006 | Narayan et al. | |
| 7,206,630 B1 | 4/2007 | Tarter | |
| 7,245,962 B2 | 7/2007 | Ciaccio et al. | |
| 7,263,397 B2 | 8/2007 | Hauck et al. | |
| 7,283,865 B2 | 10/2007 | Noren | |
| 7,289,843 B2 | 10/2007 | Beatty et al. | |
| 7,328,063 B2 | 2/2008 | Zhang et al. | |
| 7,505,810 B2 | 3/2009 | Harlev et al. | |
| 7,515,954 B2 | 4/2009 | Harlev et al. | |
| 7,751,882 B1 | 7/2010 | Helland | |
| 7,761,142 B2 | 7/2010 | Ghanem et al. | |
| 7,761,150 B2 | 7/2010 | Ghanem et al. | |
| 7,930,018 B2 | 4/2011 | Harlev et al. | |
| 7,930,020 B2 | 4/2011 | Zhang et al. | |
| 8,165,666 B1 | 4/2012 | Briggs et al. | |
| 8,715,199 B1* | 5/2014 | Macneil | A61B 5/02405 |
| | | | 600/508 |
| 9,282,910 B2* | 3/2016 | Narayan | A61B 5/042 |
| 9,398,860 B2* | 7/2016 | Macneil | A61B 5/02405 |
| 2002/0010392 A1 | 1/2002 | Desai | |
| 2003/0236466 A1 | 12/2003 | Tarjan | |
| 2004/0059237 A1 | 3/2004 | Narayan et al. | |
| 2004/0073262 A1 | 4/2004 | Lovett | |
| 2004/0243012 A1* | 12/2004 | Ciaccio | A61B 5/04011 |
| | | | 600/509 |
| 2005/0148892 A1 | 7/2005 | Desai | |
| 2005/0203502 A1 | 9/2005 | Boveja et al. | |
| 2006/0084970 A1 | 4/2006 | Beatty et al. | |
| 2006/0161206 A1* | 7/2006 | Efimov | A61B 5/0402 |
| | | | 607/5 |
| 2007/0055167 A1 | 3/2007 | Bullinga | |
| 2007/0206260 A1 | 9/2007 | Afonso | |
| 2007/0299351 A1 | 12/2007 | Harlev et al. | |
| 2008/0114258 A1 | 5/2008 | Zhang et al. | |
| 2008/0312673 A1 | 12/2008 | Viswanathan et al. | |
| 2009/0069704 A1 | 3/2009 | MacAdam et al. | |
| 2009/0099468 A1 | 4/2009 | Thiagalingam et al. | |
| 2009/0112199 A1 | 4/2009 | Zhang et al. | |
| 2009/0177071 A1 | 7/2009 | Harlev et al. | |
| 2009/0177072 A1 | 7/2009 | Harlev et al. | |
| 2009/0204164 A1 | 8/2009 | Efimov et al. | |
| 2009/0299424 A1 | 12/2009 | Narayan | |
| 2010/0094274 A1 | 4/2010 | Narayan | |
| 2010/0204592 A1 | 8/2010 | Hatib et al. | |
| 2010/0305456 A1 | 12/2010 | Braiinard, II | |
| 2011/0087121 A1 | 4/2011 | Zhang et al. | |
| 2011/0112425 A1 | 5/2011 | Muhlsteff et al. | |
| 2011/0130801 A1 | 6/2011 | Maskara et al. | |
| 2011/0251505 A1* | 10/2011 | Narayan | A61B 5/0422 |
| | | | 600/515 |
| 2011/0282227 A1 | 11/2011 | Zhang | |
| 2012/0232417 A1 | 9/2012 | Zhang et al. | |
| 2013/0006131 A1 | 1/2013 | Narayan et al. | |
| 2013/0172864 A1 | 7/2013 | Ibrahim et al. | |
| 2014/0033052 A1 | 1/2014 | Kaufman et al. | |
| 2014/0330261 A1 | 11/2014 | Arai et al. | |

FOREIGN PATENT DOCUMENTS

| | | |
|---|---|---|
| CN | 103108601 A | 5/2013 |
| RU | 2295985 C2 | 3/2007 |
| WO | 2012/092016 A1 | 7/2012 |

OTHER PUBLICATIONS

International Search Report and Written Opinion issued in PCT/US2014/021973 dated Jun. 17, 2014.

Narayan, Sanjiv M. et al., "Clinical Mapping Approach to Diagnose Electrical Rotors and Focal Impulse Sources for Human Atrial Fibrillation", Journal of Cardiovascular Electrophysiology, 2012, vol. 23, No. 5, pp. 447-566.

Extended European Search Report issued in European Application No. EP 14 77 0257 dated Nov. 7, 2016.

Houben, R.P.M., et al, "Automatic mapping of human atrial fibrillation by template matching", Heart Rhythm, vol. 3, No. 10, Oct. 1, 2006, pp. 1221-1228.

Nademanee, Koonlawee, et al., "A new approach for catheter ablation of atrial fibrillation: mapping of the electrophysiologic substrate", J. Amer.Coll.Cardiol., vol. 43, No. 11, Jun. 2, 2004, pp. 2044-2053.

Narayan, S.M., et al., "Dynamics factors preceding the initiation of atrial fibrillation in humans", Heart Rhythm, vol. 5, No. 6, Jun. 1, 2008, pp. S22-S25.

Ciaccio, Edward J. et al., "Development of Gradient Descent Adaptive Algorithms to Remove Common Mode Artifact for Improvement of Cardiovascular Signal Quality", Annals of Biomedical Engineering, vol. 35, No. 7, Jul. 2007, pp. 1146-1155.

Sornborger, Andrew, et al., "Extraction of Periodic Multivariate Signals: Mapping of Voltage-Dependent Dye Fluorescence in the Mouse Heart", IEEE Transactions on Medical Imaging, vol. 22, No, 12, Dec. 2003, pp. 1537-1549.

Sun, Yan, et al., "Characteristic wave detection in ECG signal using morphological transform", BMC Cardiovascular Disorders, vol. 5, No. 28, 2005.

(56) References Cited

OTHER PUBLICATIONS

Tai, Dean C.S., et al., "Correction of motion artifact in transmembrane voltage-sensitive fluorescent dye emission in hearts", Am, J. Physiol. Heart Circ. Physiol., vol. 287, 2004, pp. H985-H993.

Lin, Y-J, et al., "Electrophyiological Characteristics and Catheter Ablation in Patients With Paroxysmal Right Atrial Fibrillation", Circulation, Sep. 20, 2005; 112(12): 1692-1700, EPub Sep. 12, 2005.

Houben, R.P.M., et al, "Processing of Intracardiac Electrograms in Atrial Fibrillation", IEEE Engineering in Medicine and Biology Magazine, Nov./Dec. 2006, pp. 40-51.

Saksena, S., et al., "Regional Endocardial Mapping of Spontaneous and Induced Atrial Fibrillation in Patients With Heart Disease and Refractory Atrial Fibrillation", Am J Cardiol, 1999; 84:880-889.

\* cited by examiner

SYSTEM AND METHOD TO DEFINE A ROTATIONAL SOURCE ASSOCIATED WITH A BIOLOGICAL RHYTHM DISORDER

CROSS REFERENCE TO RELATED APPLICATIONS

This application is a continuation of U.S. patent application Ser. No. 14/220,662, filed on Mar. 20, 2014, now U.S. Pat. No. 9,398,860, which is a continuation of U.S. patent application Ser. No. 13/840,354, filed on Mar. 15, 2013, now U.S. Pat. No. 8,715,199, the contents of which are incorporated herein by reference in their entirety.

BACKGROUND

1. Field

The present application relates generally to biological rhythm disorders. More specifically, the present application is directed to a system and method to define a rotational source associated with a biological rhythm disorder, such as a heart rhythm disorder.

2. Brief Discussion of Related Art

Heart (cardiac) rhythm disorders are common and represent significant causes of morbidity and death throughout the world. Malfunction of the electrical system in the heart represents a proximate cause of heart rhythm disorders. Heart rhythm disorders exist in many forms, of which the most complex and difficult to treat are atrial fibrillation (AF), ventricular tachycardia (VT) and ventricular fibrillation (VF). Other rhythm disorders are more simple to treat, but may also be clinically significant including atrial tachycardia (AT), supraventricular tachycardia (SVT), atrial flutter (AFL), supraventricular ectopic complexes/beats (SVE) and premature ventricular complexes/beats (PVC).

Previously, treatment of heart rhythm disorders—particularly complex rhythm disorders of AF, VF and polymorphic VT—has been difficult because the location in the heart that harbors the source of the heart rhythm disorder could not be identified. There have been various theories of how complex rhythm disorders function and clinical applications for treating these complex rhythm disorders. However, none of the applications proved fruitful in the treatment of complex rhythm disorders.

Recently, there has been a breakthrough discovery that for the first time identified sources associated with complex heart rhythm disorders. This technological breakthrough successfully reconstructed cardiac activation information (onset times) in signals obtained from electrodes of catheters introduced into patients' heart to identify rotational activation patterns (rotational sources) that cause a large percentage of the heart rhythm disorders worldwide. Treatment of the heart rhythm disorders can thus be targeted to the rotational sources in the patients' heart to eliminate the heart rhythm disorders. Such treatment can be successfully delivered by ablation, for example.

While a rotational source of a complex heart rhythm disorder can be identified as described above, the extent or breadth of the propagation of the rotational source and its likely center of rotation have not been defined. In some instances, a rotational source may have one or more diffuse sections (activation wave fronts) that generally appear to rotate around a subjective rotation center, but tend to spread out diffusely about a section of the patient's heart. While the diffuse activation wave fronts are associated with the source of the complex rhythm disorder, they may contribute insignificantly to driving the heart rhythm disorder than one or more other activation wave fronts of the rotational source.

There are no known systems or methods to define a rotational source associated with a heart rhythm disorder, including a rotational path and a likely center of rotation associated with the rotational source.

SUMMARY

The present disclosure is applicable to various rhythm disorders, including heart rhythm disorders, as well as other biological rhythm disorders, such as neurological seizures, esophageal spasms, bladder instability, irritable bowel syndrome, and other biological disorders for which biological activation information has to be reconstructed to permit determination, diagnosis, and/or treatment of a rotational source causing the biological rhythm disorders. It is particularly useful, however, in complex rhythm disorders of the heart, in order to find the core of the rotational sources of the disorders such that they can be treated with precision and expediency.

Among the advantages of the present disclosure is the ability to use reconstructed cardiac (or biological) activation information associated with a rotational source of the rhythm disorder such that a determination of a core of the rotational source can be determined and treated.

Another advantage is that the present invention provides a system and a method, which can be carried out rapidly while a sensing device—such as a catheter having sensors thereon—is used in or near the patient and can be followed by treatment of cardiac tissue to ameliorate the rhythm disorder and in many cases cure the rhythm disorder. Treatment may thus occur immediately upon computing the core of the source of the rhythm disorder, since it will provide the location in the patient of the core that is driving the rotational source.

Still another advantage of the present disclosure is that precise identification of the core for the rotational source can help eliminate the heart rhythm disorder, while also helping to limit or spare the destruction of otherwise healthy heart tissue of the patient that may only insignificantly contribute to driving the source of the heart rhythm disorder.

As used herein, reconstructed activation information is signal data of cardiac or biological signals each of which has been processed to identify activation onset times at a sensor location distinct from nearby or adjacent sensor locations for one or more beats of a biological or cardiac rhythm disorder.

As used herein, activation onset time is a time point at which activation commences in a cell or tissue of a patient, as opposed to other time points during activation.

As used herein, activation is a process whereby a cell commences its operation from a quiescent (diastolic) state to an active (electrical) state.

In accordance with an embodiment or aspect, a method of defining a rotational source associated with a heart rhythm disorder is disclosed. A plurality of center locations of wave fronts are calculated at a plurality of time points associated with the heart rhythm disorder. A rotational path that connects the plurality of center locations is then determined. Thereafter, a clinical representation that identifies a region of heart tissue associated with the rotational path is generated.

The method can also include determination of a likely core associated with the rotational path. A plurality of relative diffusion shapes associated with the plurality of center locations is calculated. A plurality of intersecting points of a smallest relative diffusion shape and other relative diffusion shapes is determined within the rotational path. A bounded polygon of the intersecting points is defined as the likely core.

In accordance with an embodiment or aspect, a system to define a rotational source associated with a heart rhythm disorder is disclosed. The system includes a computing device and a machine-readable medium to store instructions that, when executed by the computing device, cause the computing device to perform certain operations. The operations include calculating a plurality of center locations of wave fronts at a plurality of time points associated with the rotational source. The operations also include determining a rotational path that connects the plurality of center locations. The operations further include generating a clinical representation that identifies a region of heart tissue associated with the rotational path.

The computing device can also perform operations for determining a likely core associated with the rotational path. These operations include calculating a plurality of relative diffusion shapes associated with the plurality of the center locations. These operations also include determining a plurality of intersecting points of a smallest relative diffusion shape and other relative diffusion shapes within the rotational path. These operations further include defining a bounded polygon of the intersecting points as the likely core.

In accordance with still another embodiment or aspect, a tangible computer-readable medium that stores instructions which, when executed by a processor, cause the processor to perform operations for defining a rotational source associated with a heart rhythm disorder, is disclosed. The operations include calculating a plurality of center locations of wave fronts at a plurality of time points associated with the rotational source. The operations also include determining a rotational path that connects the plurality of center locations. The operations further include generating a clinical representation that identifies a region of heart tissue associated with the rotational path The tangible computer-readable medium can also store instructions which, when executed by a processor, cause the processor to perform operations for determining a likely core associated with the rotational path. These operations include calculating a plurality of relative diffusion shapes associated with the plurality of the center locations. These operations also include determining a plurality of intersecting points of a smallest relative diffusion shape and other relative diffusion shapes within the rotational path. These operations further include defining a bounded polygon of the intersecting points as the likely core.

The above-described embodiments or aspects can further access reconstructed signal data having activation onset times associated with voltages at the plurality of time points. The signal data can be transformed from spline-sensor references to locations having associated coordinates.

The above-described embodiments or aspects can further determine the wave fronts to include adjacent locations having at least a threshold voltage level surrounded by locations below the threshold voltage level. The threshold voltage level can be a predetermined percentage of a highest voltage.

The above-described embodiments or aspects can further determine a convex hull around the rotational path, such that the plurality of intersecting points of the smallest relative diffusion shape and other relative diffusion shapes can be determined to be inside the convex hull in order to define the likely core.

The above-described embodiments or aspects can further include a determination of a center location of a wave front.

All first coordinates of locations associated with the wave front are averaged to generate a first average coordinate. All second coordinates of the locations associated with the wave front are averaged to generate a second average coordinate. Thereafter, center location of the wave front is defined as a location identified by the first average coordinate and the second average coordinate.

The above-described embodiments or aspects can further calculate a relative diffusion shape of a wave front. The calculation can include determining distances from locations in the wave front to a center location of the wave front, and calculating a circle having a radius equal to a predetermined multiplier multiplied by a standard deviation of the distances. The predetermined multiplier can be equal to two.

These and other purposes, goals and advantages of the present application will become apparent from the following detailed description read in connection with the accompanying drawings.

BRIEF DESCRIPTION OF THE DRAWINGS

Some embodiments or aspects are illustrated by way of example and not limitation in the figures of the accompanying drawings in which.

DETAILED DESCRIPTION

A system and method to define a rotational source of a biological rhythm disorder, such as a heart rhythm disorder, is disclosed herein. In the following description, for the purposes of explanation, numerous specific details are set forth in order to provide a thorough understanding of example embodiments or aspects. It will be evident, however, to one skilled in the art, that an example embodiment may be practiced without all of the disclosed specific details.

Figure 1:
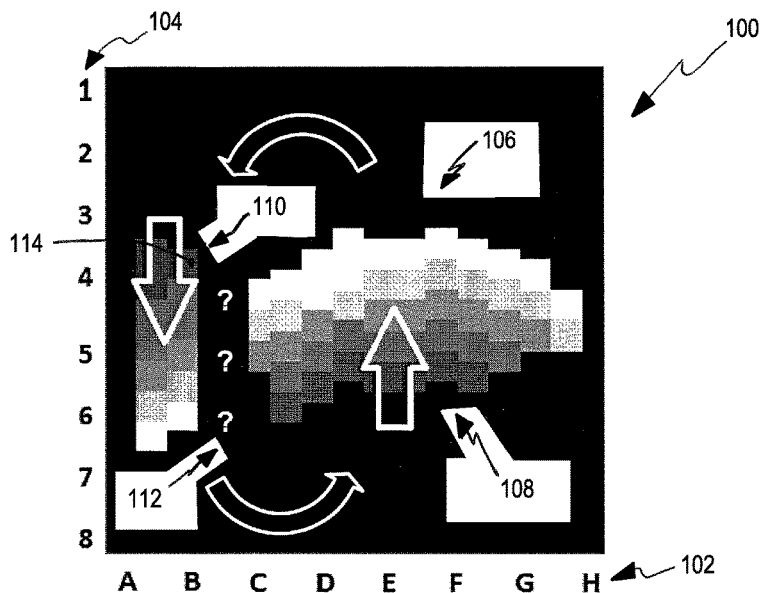
FIG. 1 illustrates an example graphical mapping of an example rotational source associated with a heart rhythm disorder in a patient.

FIG. 1 illustrates an example graphical mapping 100 of an example rotational source 106 associated with a heart rhythm disorder in a patient. For example, the rotational source 106 is a source of a heart rhythm disorder in a right atrium of the patient's heart that is observed to progress in a counter-clockwise rotational pattern about a subjective rotation center 112 (one or more of the locations marked with question marks), which can be evaluated by a physician to be along the electrode reference 104, anywhere between about electrodes 4-5-6, and along the spline reference 102, anywhere between about splines B-C, of a basket-type catheter (not shown) introduced into the patient's heart. It is noted that the rotational sources of different heart rhythm disorders can be disposed at different locations in different chambers of the heart and can rotate in different directions (e.g., clockwise) about various centers of rotation.

The example rotational source 106 can include a plurality of activation mappings 108, 110 that progress in the counter-clockwise rotational pattern about the subjective rotational center 112 over time of a cycle, e.g., 100 ms-300 ms. Each of the activation mappings 108, 110 can include elements 114 that represent a charge level (or voltage level) of a sensor at a spline reference 102 and a sensor reference 104. The activation mappings 108, 110 represent reconstructed activation information (reconstructed signal data of cardiac signals) identifying activation onset times at a plurality of sensors for one or more beats of a cardiac rhythm disorder. For example, the activation mappings 108, 110 can be generated by the system and method for reconstructing cardiac activation information patented in U.S. Pat. No. 8,165,666, which is incorporated herein by reference in its entirety.

Figure 11:
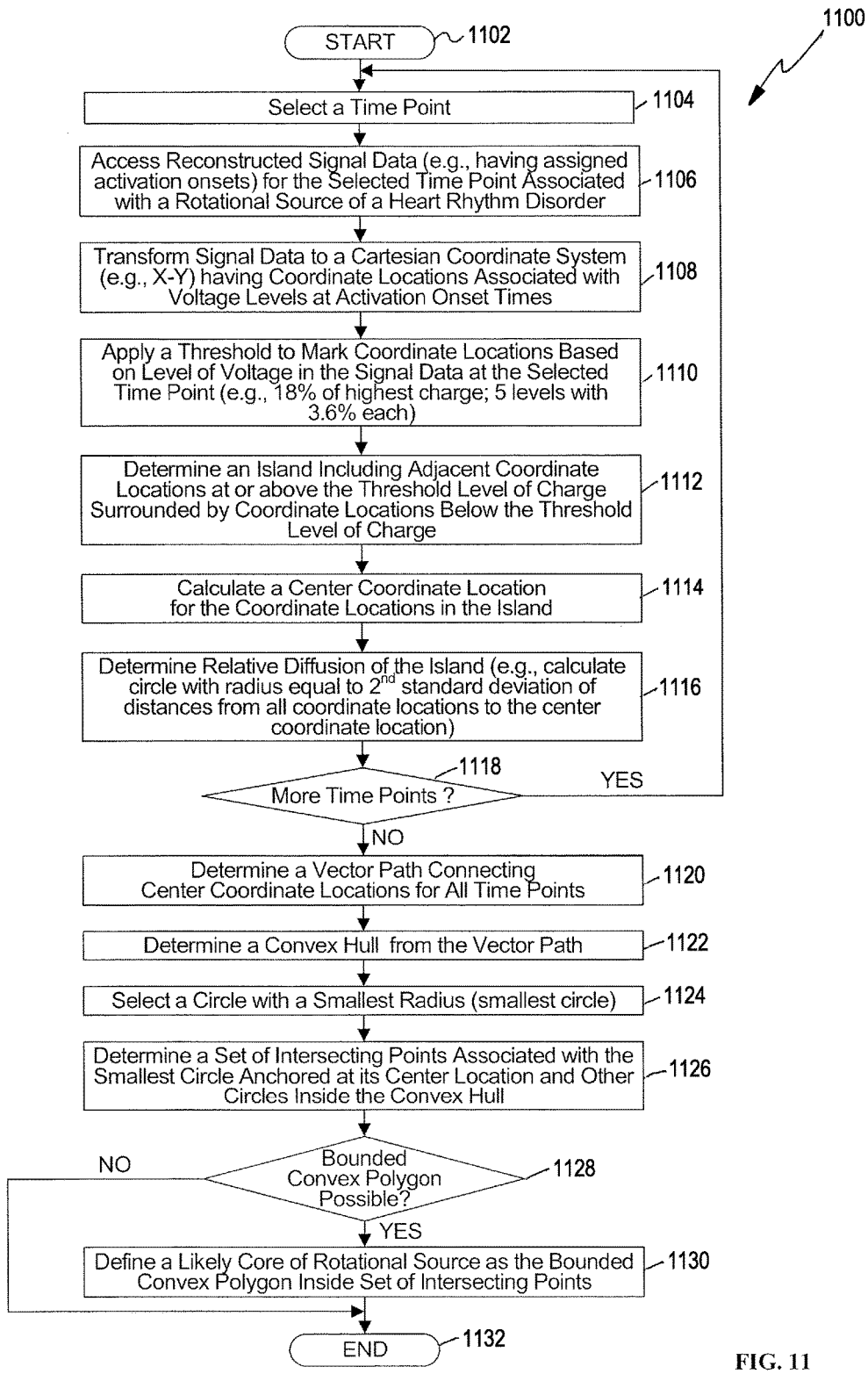
FIG. 11 is a flowchart that illustrates an example method of determining a rotational path and identifying a likely core associated with a rotational source of a biological rhythm disorder, such as a rotational source of the heart rhythm disorder illustrated in FIG. 1.

For example, the activation mappings 108, 110 (or activation wave fronts) can be a monophasic action potential (MAP) voltage representation generated for multiple processed cardiac signals shown in FIG. 11 of the '666 patent. Specifically, multiple cardiac signals are processed as described in the '666 patent and MAP representations are generated based on these processed signals. The electrical activity of all the MAP representations can be mapped in a sequence showing the example activation mappings 108, 110 at different time points, e.g., activation mapping 108 being earlier than activation mapping 110. While only two activation mappings 108, 110 (or activation wave fronts) are shown for clarity and brevity of this disclosure, it should be noted that additional activation mappings can be part of the rotational source 106 about the subjective rotation center 112.

Similarly, other systems and methods that can reconstruct cardiac or biological activation information to generate rotational sources can be used as input into the present system and method of determining a rotational path and identifying a likely core of rotation associated with these rotational sources.

In some instances, a rotational source 106 may have one or more diffuse sections, such as activation wave front 108. The activation wave front 108 generally rotates around the subjective rotation center 112, spreading out diffusely about a section of the patient's heart, and appears to contribute insignificantly to driving the heart rhythm disorder than one or more other activation wave fronts 110 of the rotational source 106. Accordingly, FIGS. 2-11 described below in greater detail will elucidate how to computationally determine a rotational path and identify a likely core of the rotational source 106 more precisely than the subjective rotation center 112, as described hereinabove with reference to FIG. 1.

Figure 2:
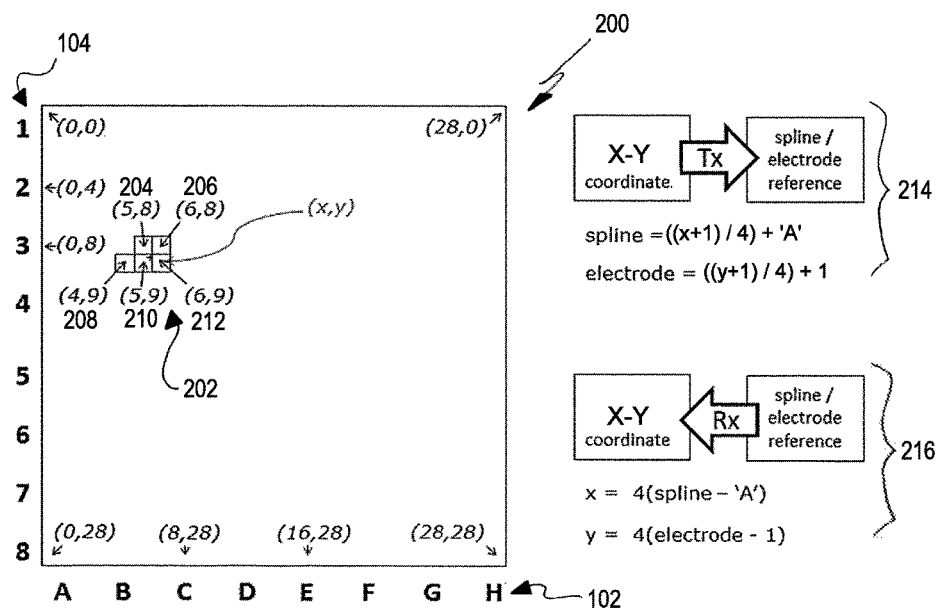
FIG. 2 illustrates an example x-y coordinate graphical mapping of a spline-sensor element in FIG. 1.

FIG. 2 illustrates an example Cartesian (x-y coordinate) graphical mapping 200. The Cartesian graphical mapping 200 presents an example method of transforming reconstructed signal data of cardiac signals from the spline/electrode references 102, 104 illustrated in the graphical mapping 100 to the x-y coordinates illustrated in this Cartesian graphical mapping 200, which are used in one or more calculations and/or determinations described with reference to FIGS. 3-11.

For example, the Cartesian graphical mapping 200 extends from x-y (0, 0) to x-y (28, 28). The example plurality of x-y coordinate locations 202 can represent the element 114 of activation wave front 110 in FIG. 1. The coordinate locations 202 (including locations 204-212) and their associated charge (voltage) levels can be interpolated from the element 114 of the graphical mapping 100. Accordingly, the other elements of the activation wave fronts 108, 110 in FIG. 1 can be similarly transformed to the Cartesian coordinates.

A transformation Tx 214 can transform an x-y coordinate location to a spline-electrode reference. For example, a location at an x-y coordinate (4, 8) can be transformed to the following spline-electrode reference:

$$\text{spline}=((x+1)/4)+A=((4+1)/4)+A=1.25+A=B; \text{ and}$$

$$\text{electrode}=((y+1)/4)+1=((8+1)/4)+1=2.25+1=3.25=3.$$

In some embodiments, the spline-electrode reference values are rounded to a nearest whole spline and whole electrode. In various other embodiments, a fractional spline can be utilized for certain applications.

A transformation Rx 216 is a reverse of the transformation Tx 214. The transformation Rx 216 can transform the foregoing spline-electrode reference to an x-y coordinate location. For example, the spline-electrode location B-3 can be transformed to the following x-y coordinate location:

$$x=4(\text{spline-}A)=4(B-A)=4(1)=4; \text{ and}$$

$$y=4(\text{electrode-}1)=4(3-1)=4(2)=8.$$

In the foregoing examples, the electrodes have the benefit of actual numbers assigned to them. However, the splines have letters assigned. To perform mathematical operations set forth above, the splines are represented by numbers as follows: A, B . . . H represented by 1, 2 . . . 8. Accordingly, the following spline calculations can be easily performed:

$$A-A=(1-1)=0;$$
$$B-A=(2-1)=1;$$
$$\ldots$$
$$H-A=(8-1)=7.$$

The spline representations can also be used to perform other spline calculations, such as addition, as well as other mathematical calculations.

Figure 3:
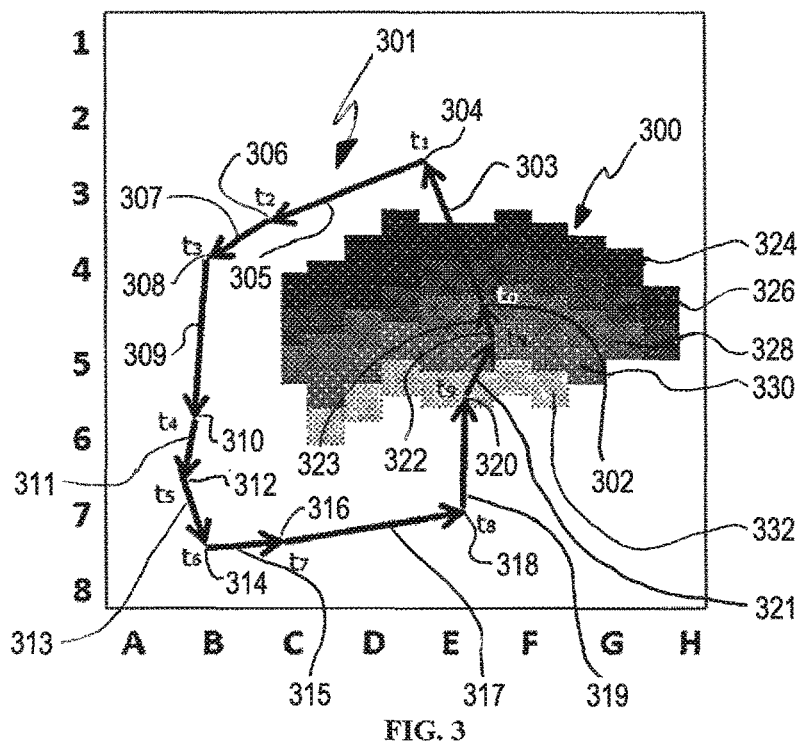
FIG. 3 illustrates a first example activation wave front of a rotational source illustrated in FIG. 1 at a first example time point, as transformed into a first wave front (island) with a threshold applied to associated voltages.

FIG. 3 illustrates the sample activation wave front 108 of the rotational source 106 illustrated in FIG. 1 at an example time point $T_0$, as transformed into a Cartesian wave front (island) 300 with threshold applied to the associated charges (voltages). While the island 300 looks similar to the activation wave front 108, it should be noted that only those Cartesian coordinate locations are represented that are adjacently located and are above a charge (voltage) threshold, as described in greater detail below.

More specifically, a threshold of top 18% is applied to the charges (voltages) of elements in the activation wave front 108. Accordingly, when spline-electrode references of the activation wave front 108 are transformed into associated locations of the Cartesian wave front (island) 300, the only locations that are identified and marked for inclusion in the island 300 and used in later calculations, as described herein, are those adjacent locations that are above the threshold charge (voltage). The locations are marked with the threshold charge (voltage) level. More specifically, the adjacent locations that are above the threshold define the island of locations which are above the threshold with other locations surrounding the island which are below the threshold.

Moreover, five charge (voltage) levels 324-332 can be defined in the threshold, with each level being 3.6% of the threshold (e.g., top 18% of charges for the island). Specifically, the highest charge level 324 is defined as [0%-3.6%] of the top 18% of charges (voltages) in the activation wave front 108. Charge levels 326, 328, 330 and 332 are defined, respectively, as [3.6%-7.2%], [7.2%-10.8%], [10.8%-14.4%], and [14.4%-18.0%]. While a threshold of 18% is used, other thresholds can be defined.

As further illustrated in FIG. 3, eleven (11) time points $T_0$-$T_N$ are associated with the rotational source 106 as it completes a cycle of activation. Each of the time points can be about 10 ms to about 30 ms apart, for a total time of about 100 ms to about 300 ms, as described herein in association with a cycle of a heart rhythm disorder. A larger number of time points can be used in association with a cycle of a heart rhythm disorder. For example, each time point can be about 1 ms apart, or another higher time interval apart.

The x-y coordinate locations that contribute to the island 300 are averaged to compute a center location 302 at the example time point $T_0$. The calculation of the center location at a time point will be illustrated in greater detail with reference to FIG. 5 below. Similarly, center locations 304, 306 . . . 322 are calculated for the islands at the time points $T_1$-$T_N$.

The center locations 302, 304 . . . 322 in the islands 300 and others (all islands not shown) at the time points $T_0$-$T_N$ over a course of a full cycle define a vector path 301 that is associated with a likely core of the rotational source 106 illustrated in FIG. 1. As illustrated in FIG. 3, the vector path 301 includes vectors 303, 305 . . . 323 extending between and contacting the center locations 302, 304 . . . 322.

Figure 4:
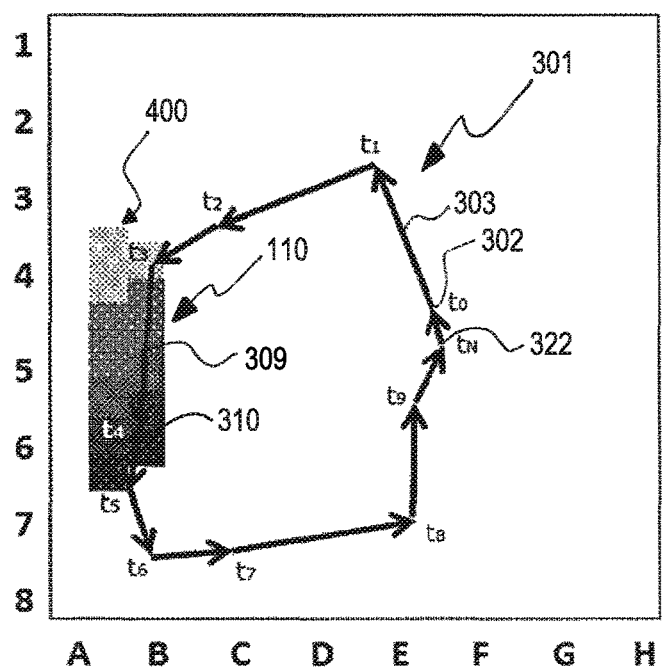
FIG. 4 illustrates a second example activation wave front of a rotational source illustrated in FIG. 1 at a second example time point, as transformed into a second wave front (island) with a threshold applied to associated voltages.

FIG. 4 illustrates the sample activation wave front 110 of the rotational source 106 illustrated in FIG. 1 at an example time point $T_4$, as transformed into Cartesian wave front (island) 400 with a threshold applied to the associated charges (voltages). Similar computations are performed to define the island 300, as described hereinabove with reference to island 400 in FIG. 3.

Specifically, the x-y coordinate locations that contribute to the island 400 are averaged to compute a center location 310 at the example time point $T_4$. As previously described, the center locations 302, 304 . . . 322 in the islands 300, 400 and others (all islands not shown) at the time points $T_0$-$T_N$ over a course of the full cycle define the vector path 300 that is associated with a likely core of the vector path 301, e.g., a likely core of the rotational source 106 illustrated in FIG. 1.

Figure 5:
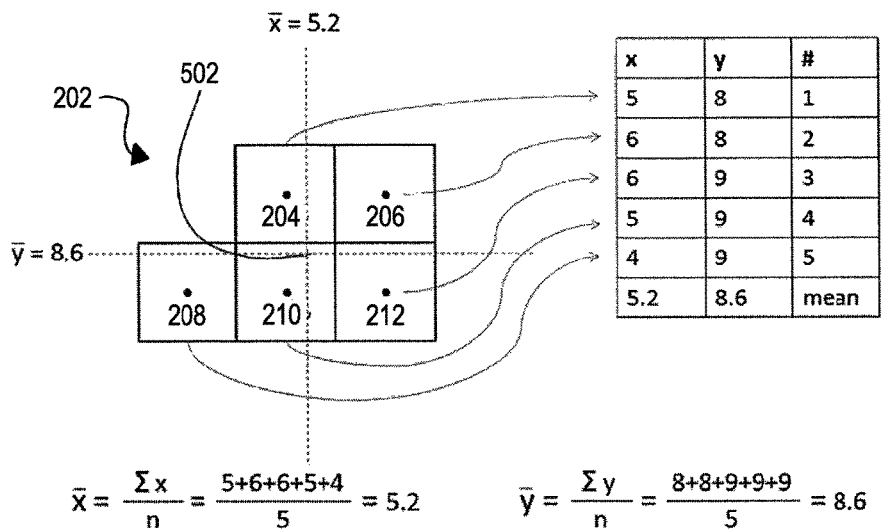
FIG. 5 illustrates the averaging of x-y coordinate locations that contribute to an example island represented by the x-y coordinate graphical mapping in FIG. 2.

FIG. 5 illustrates the averaging of x-y coordinate locations that contribute to an example island, represented by the graphical mapping 200 illustrated in FIG. 2.

As particularly illustrated in FIG. 5, the x-coordinates of the locations 204-212 in the island 200 (as set forth in FIG. 2) are averaged to determine a mean x-coordinate of 5.2. Similarly, the y-coordinates of the locations 204-212 in the island 200 (as set forth in FIG. 2) are averaged to determine a mean y-coordinate of 8.6. It should be noted that the x-y coordinates of the locations 204-212 represent their centers.

Accordingly, the calculated averages of the x-coordinates and the y-coordinates of locations in the island 200 define a center location 502 for the island as an x-y coordinate location (5.2, 8.6).

Figure 6:
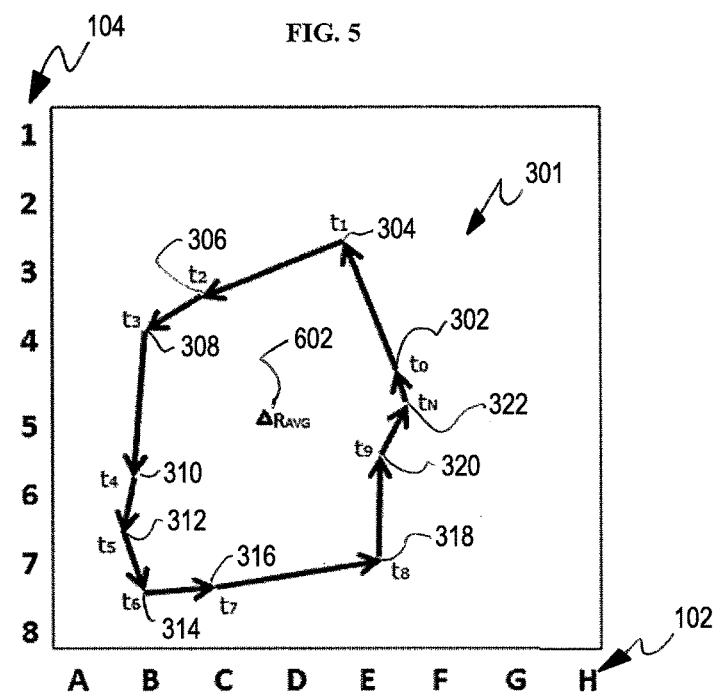
FIG. 6 illustrates an average center location based on calculated center locations of the constituent islands in FIGS. 3, 4 inside a vector path.

FIG. 6 illustrates an average center location 602 based on the calculated center locations 302, 304 . . . 322 of the constituent islands 300, 400 in FIGS. 3, 4 and others islands (not shown) inside the vector path 301.

As illustrated in FIG. 6, the average center location 602 based on the center locations 302, 304 . . . 322 at the time points $T_0$-$T_N$ identifies an x-y coordinate location inside the vector path 301, which is transformed into a spline-electrode reference (using FIG. 2) to be approximately between splines C-D and electrode 5, as marked by a location identified by a triangle $R_{AVG}$.

It is clear that a number of diffuse islands, such as the island 300 of FIG. 3, tend to bias the computed average of the center locations of all the islands towards an approximate center location ($R_{AVG}$) of the vector path 301, rather than a location about the subjective rotation center 112 that was expected to be between about splines B-C (and electrodes 4-5-6), as described hereinabove with reference to in FIG. 1. The description hereinbelow with FIGS. 7-10 illustrates a method to eliminate the biasing produced by the diffused islands, such as island 300.

Figure 7:
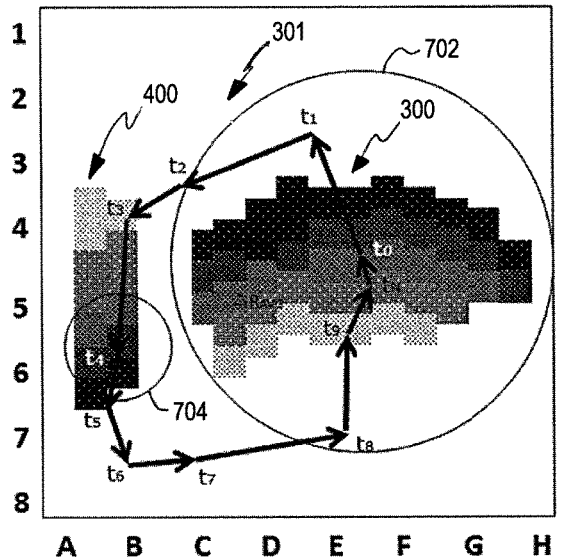
FIG. 7 illustrates relative spatial diffusions of the islands in relation to the vector path which have center locations that form the vector path.

FIG. 7 illustrates relative spatial diffusions 702, 704 of the islands 300, 400 in relation to the vector path 301 illustrated in FIGS. 3, 4, as well as others islands (not shown) which have center locations that form the vector path 301.

It has been determined that the islands (wave fronts) of the source of the rhythm disorder that are relatively spatially distributed (diffused) over a relatively wide portion of the heart (e.g., island 300) in relation to the vector path 301 can include locations that are influenced not only by a likely core of the source of the heart rhythm disorder, but also by other portions of the heart that are potentially unrelated to an electrical pathway associated with the likely core of the source of the heart rhythm disorder.

It has further been determined that those locations of the islands (wave fronts), which are focused in a relatively smallest spatial distribution (e.g., island 400) in relation to the vector path 301, represent a focused link of continuity associated with an electrical circuit driven by the likely core of the source of the heart rhythm disorder and therefore are associated with the electrical pathway needed to sustain the source of the heart rhythm disorder.

An example method of calculating relative spatial diffusion in relation to the vector path 301 is described below in relation to FIG. 8. Other methods of determining the relative diffusion can be utilized.

Figure 8:
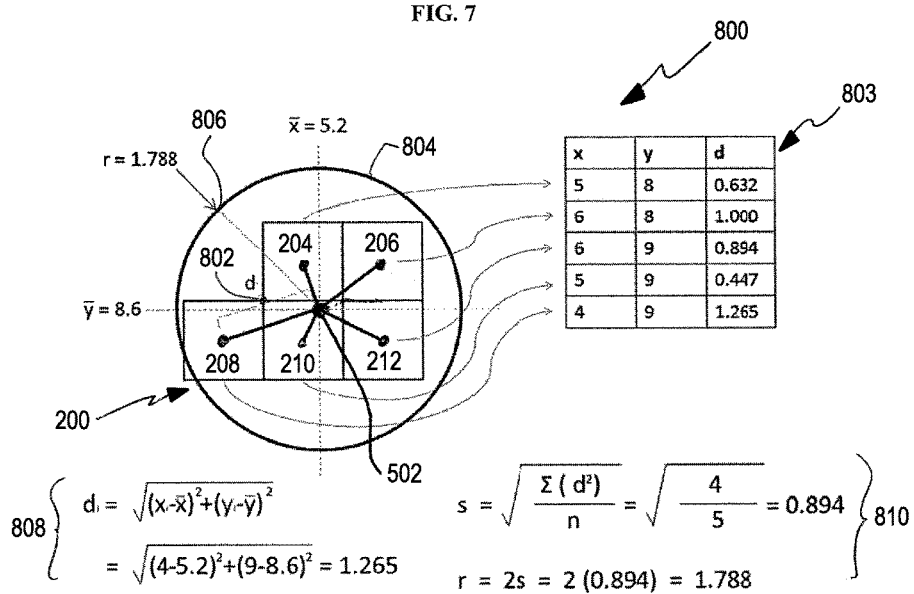
FIG. 8 illustrates an example method of calculating a relative spatial diffusion of an island in relation to the vector path.

FIG. 8 illustrates an example method 800 of calculating a relative spatial diffusion of an island in relation to a vector path. In this example, the mapping 200 of FIG. 2 is considered to be an island (wave front) whose center location 502 at the coordinate location (5.2, 8.6) lies along a vector path.

As illustrated in FIG. 5, the x-coordinates of the locations 204-212 in the island 200 (as set forth in FIG. 2) are averaged to determine a mean x-coordinate of 5.2. Similarly, the y-coordinates of the locations 204-212 in the island 200 (as set forth in FIG. 2) are averaged to determine a mean y-coordinate of 8.6. Accordingly, the calculated center location 502 for the island 200 is the x-y coordinate pair (5.2, 8.6).

A distance d 802 is determined for each of the locations 204-212. The distance d 802 represents a distance from the x-y coordinate of each location to the calculated center location 502 of the island 200. For example, an equation 808 illustrates a distance calculation 804 which calculates the distance d 802 from the location 208 (4, 9) to the center location 502 (5.2, 8.6) to be d=1.265. Similarly, the distances d are also calculated for all other constituent locations of the island 200. The distances d for all locations 204-212 of the island 200 are given in the table 803.

The relative diffusion of the island 200 is represented by a circle 804 having a radius 806 from the center location 502 that is equal to the second standard deviation of distances from all locations 208-212 to the center location 502 of the island 200. For example, the radius 806 is given by an equation 810 in which a standard deviation of all distances is s=0.894 and a second standard deviation is 2s=1.788. Accordingly, the relative diffusion of the island 200 is represented by a circle having a radius of 1.788 from the center location 502 (5.2, 8.6).

The relative diffusions 702, 704 of islands 300, 400 in relation to the vector path 301 illustrated in FIG. 7, as well as others islands (not shown) which have center locations that form or lie along the vector path 301, can be calculated using the example method 800 described hereinabove.

Figure 9:
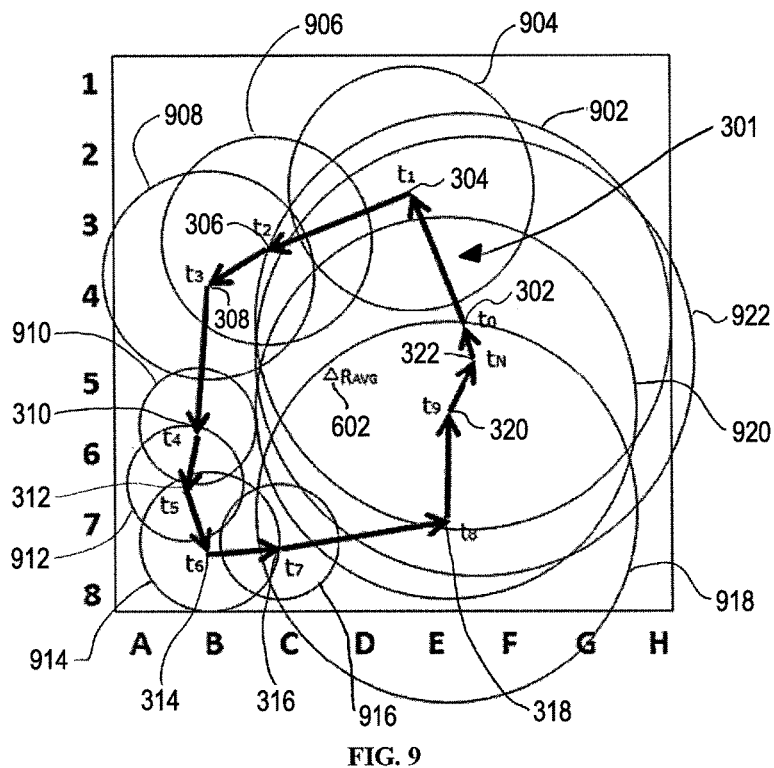
FIG. 9 illustrates relative diffusions of islands in FIG. 7 relative to their center locations at respective time points in relation to the vector path.

FIG. 9 illustrates relative diffusions 902-922 of islands 300, 400 of FIG. 7 relative to their center locations 302, 310 at respective time points $t_0$, $t_4$, and other islands (not shown) in relation to their center locations 304-308, 312-322 at respective time points $t_1$-$t_3$, $t_5$-$t_N$, all of the foregoing in relation to the vector path 301.

As illustrated, the spatial distributions 902-922 are represented by the computed circles 902-922 whose radii represent the relative distributions or diffuseness of the islands at the time points $t_0$-$t_N$ in relation to the vector path 301. The relevance of each of the circles 902-922 to the likely core of the rotational source (e.g., subjective center of rotation 112 illustrated in FIG. 1) is inversely proportional to the size of each of the circles 902-922 at a respective time point $t_0$-$t_N$. However, the average location $R_{AVG}$ 602 is skewed toward the larger circles (with larger radii). Accordingly, it is expected that the likely core of the rotational source lies at a location that is toward the smaller circles 910-916.

Figure 10:
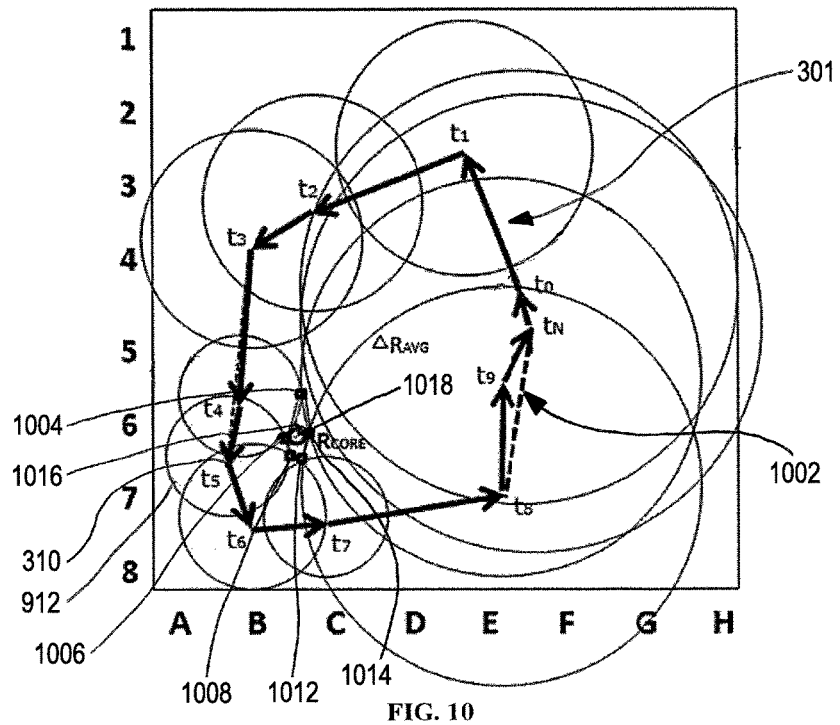
FIG. 10 illustrates determination of an example core associated with a rotational source of a heart rhythm disorder illustrated in FIG. 1.

FIG. 10 illustrates determination of an example likely core 1018 associated with a rotational source 106 of a heart rhythm disorder illustrated in FIG. 1.

As particularly illustrated in FIG. 10, the vector path 301 connects the center locations 302-322 (illustrated in FIG. 3) for all time points $t_0$-$t_N$ in relation to the vector path 301. A convex hull 1002 is determined for the vector path 301. The convex hull 1002 represents a convex shape around the vector path 301 constructed from the center locations 302-322 at the time points $t_0$-$t_N$.

More specifically, a convex hull is a smallest convex polygon that surrounds a set of (x,y) coordinate locations. The convex hull can be thought of as a shape formed by stretching a rubber band around the set of the coordinate locations to define a set of outside perimeter edges. Coordinate locations that are not located on the outside perimeter edges are, therefore, internal and do not contribute to stretching of the shape.

Computational geometry includes several established algorithms to construct a convex hull. An example of such algorithms includes a so-called giftwrap algorithm, which finds shortest flat sides of a convex shape that surround a set of points. The giftwrap algorithm operates by folding a hypothetical sheet of wrapping paper counter-clockwise around outside edges of the set of points until one full revolution around the set of points is completed (e.g., such that a last side touches a first side), resulting in a convex polygon (convex hull).

Accordingly, the convex hull 1002 is determined to smooth the perimeter of the vector path 301 by ignoring internal excursions of the vector path 301 that zigzag to the interior of outside perimeter edges, e.g., vectors 303, 305 . . . 323 associated with the vector path 301. A degree of difference between the shape of the vector path 301 and the convex hull 1002 around that vector path 301 can indicate a measure of the eccentricity associated with the vector path 301 (e.g., many internal excursions would indicate a more erratic vector path 301).

A circle having the smallest radius (e.g., smallest circle 912) is selected with its center location 310 (illustrated in FIG. 3) as an anchor. A set of intersecting points 1004-1014 is determined inside the convex hull 1002—starting with the smallest circle 912 and the adjacent circles 910, 914, 916, 918 and 920—which define an inscribed polygon 1016 inside the convex hull 1002.

Thereafter, the likely core $R_{core}$ 1018 of the rotational source 106 associated with the heart rhythm disorder illustrated in FIG. 1 is defined as a subset of the intersecting points 1004-1014 (e.g., inscribed polygon 1016), which represents a bounded convex polygon inside the set of intersecting points 1004-1014 (inscribed polygon 1016) and within the convex hull 1002.

FIG. 11 is a flowchart that illustrates an example method 1100 of determining a rotational path and identifying a likely core that are associated with a rotational source of a biological rhythm disorder, such as a rotational source 106 of the heart rhythm disorder illustrated in FIG. 1. The example method 1100 can be performed by the computing system 1200 described hereinbelow in greater detail with reference to FIG. 12.

More specifically, the example method 1100 starts at operation 1102 at which reconstructed signal data (e.g., having assigned activation onset times) associated with the rotational source 106 of a heart rhythm disorder in FIG. 1 is provided or can be accessed by the example method 1100. At operation 1104, a time point is selected, such as a time point $T_0$ of time points $T_0$-$T_N$, as illustrated in FIG. 3.

At operation 1106, the reconstructed signal data is accessed for the selected time point. At operation 1108, the signal data is transformed from spline-electrode references to Cartesian coordinate locations that are associated with voltage levels at the activation onset times. Example transformations are described with reference to FIG. 2.

A threshold level is applied to the coordinate locations at operation 1110, with the coordinate locations being marked based on a top level of charge (voltage) in the signal data at the selected point of time, e.g., $T_0$. As described herein with reference to FIG. 3, the threshold level representing a top 18% of charges or another threshold level can be applied to the coordinate locations.

At operation 1112, an island (wave front) including adjacent coordinate locations at or above the threshold level that is surrounded by coordinate locations below the threshold level is determined. Example island determinations are described with reference to FIGS. 3 and 4. At operation 1114, a center location is calculated for the coordinate locations in the island. An example calculation of a center location in an island is described with reference to FIG. 5.

A relative diffusion of the island is determined at operation 1116. The relative diffusion can be a circle having a radius representative of the diffusion of locations in the island. An example calculation of the relative diffusion is described with reference to FIG. 8.

It should be noted that the foregoing data that is accessed, transformed, determined and calculated can be stored (such as in computer memory or storage device) for later use in accordance with the example method 1100.

At operation 1118, a determination is made as to whether there are more time points to process, such as time points $T_1$-$T_N$. If there are more time points to process as determined at operation 1118, the operations 1104-1116 are repeated for the next time point (e.g., time point $T_1$) and so on until all time points ($T_0$-$T_N$) have been processed. After a determination is made that there are no more time points to process at operation 1118, then the method 1100 continues at operation 1120.

Thereafter, at operation 1120 a vector path that connects the center locations at all of the time points ($T_0$-$T_N$) is determined. An example determination of the vector path is described with reference to FIG. 3. At operation 1122, a convex hull is determined from the vector path. An example determination of a convex hull is described with reference to FIG. 10.

A circle having a smallest radius (smallest circle) is selected at operation 1124. Then, a set of intersecting points (e.g., inscribed polygon) associated with the smallest circle anchored at its center location and other circles inside the convex hull is determined at operation 1126. At operation 1128, a determination is made as to whether formation of a bounded convex polygon is possible inside the set of intersecting points within the convex hull. If it is determined that the bounded convex polygon can be formed, then the method 1100 continues at operation 1130. Alternatively, the method continues at operation 1132.

At operation 1130, a likely core of the rotational source 106 of the heart rhythm disorder of FIG. 1 is defined as a subset of the intersecting points that form the bounded convex polygon inside the convex hull. An example of operations 1124-1130 is also described with reference to FIG. 10. At operation 1132, the method 1100 ends.

In operation, the rotational source 106 of the heart rhythm disorder illustrated in FIG. 1, as defined according to the foregoing disclosure, can be treated in the patient's heart to eliminate the heart rhythm disorder. For example, heart tissue of the patient on or within the defined rotational path 301 can thus be targeted for treatment. In cases where the likely core 1018 is identified, treatment can be targeted to heart tissue on or within the likely core 1018, sparing heart tissue outside the likely core 1018. In various cases, a margin beyond the rotational path 301 or the likely core 1018 can be established for treatment purposes. For example, a region of heart tissue slightly larger (e.g., a millimeter or several millimeters) than the rotational path 301 or the likely core 1018 can be targeted for treatment.

The treatment can be successfully delivered to the targeted heart tissue (rotational path 301 or likely core 1018—with/without margin) by ablation, for example. Other treatments of the targeted heart tissue are of course possible, e.g., various energy sources (including but not limited to radiofrequency, cryoenergy, microwave, and ultrasound), gene therapy, stem cell therapy, pacing stimulation, drug or other therapy.

Figure 12:
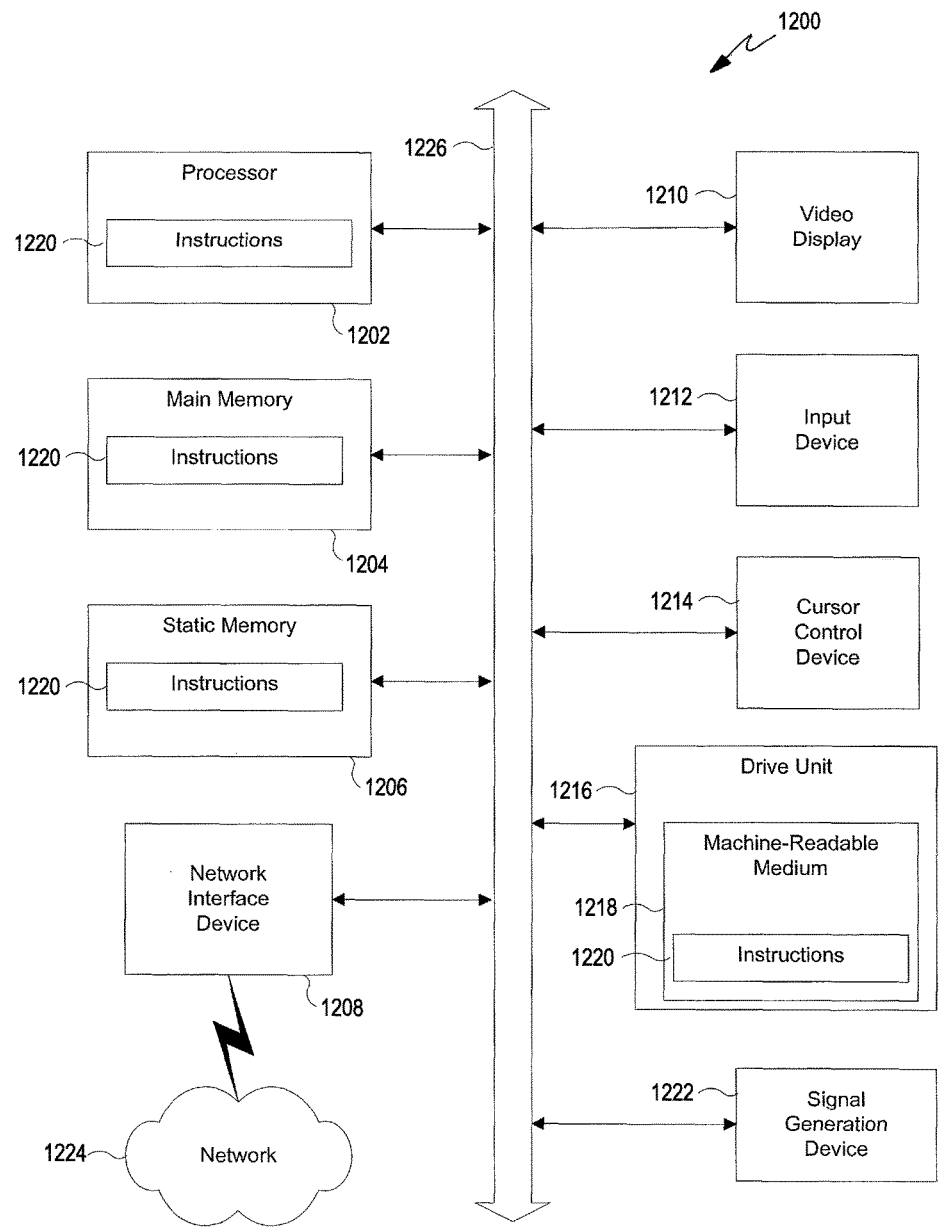
FIG. 12 is a block diagram of an illustrative embodiment of a general computing system.

FIG. 12 is a block diagram of an illustrative embodiment of a general computing system 1200. The computing system 1200 can include a set of instructions that can be executed to cause the computing system 1200 to perform any one or more of the methods or computer based functions disclosed herein. The computing system 1200, or any portion thereof, may operate as a standalone device or may be connected, e.g., using a network 1224 or other connection, to other computing systems or peripheral devices.

The computing system 1200 may also be implemented as or incorporated into various devices, such as a personal computer (PC), a tablet PC, a personal digital assistant (PDA), a mobile device, a palmtop computer, a laptop computer, a desktop computer, a communications device, a control system, a web appliance, or any other machine capable of executing a set of instructions (sequentially or otherwise) that specify actions to be taken by that machine. Further, while a single computing system 1200 is illustrated, the term "system" shall also be taken to include any collection of systems or sub-systems that individually or jointly execute a set, or multiple sets, of instructions to perform one or more computer functions.

As illustrated in FIG. 12, the computing system 1200 may include a processor 1202, e.g., a central processing unit (CPU), a graphics-processing unit (GPU), or both. Moreover, the computing system 1200 may include a main memory 1204 and a static memory 1206 that can communicate with each other via a bus 1226. As shown, the computing system 1200 may further include a video display unit 1210, such as a liquid crystal display (LCD), an organic light emitting diode (OLED), a flat panel display, a solid state display, or a cathode ray tube (CRT). Additionally, the computing system 1200 may include an input device 1212, such as a keyboard, and a cursor control device 1214, such as a mouse. The computing system 1200 can also include a disk drive unit 1216, a signal generation device 1222, such as a speaker or remote control, and a network interface device 1208.

In a particular embodiment or aspect, as depicted in FIG. 12, the disk drive unit 1216 may include a machine-readable or computer-readable medium 1218 in which one or more sets of instructions 1220, e.g., software, can be embedded, encoded or stored. Further, the instructions 1220 may embody one or more of the methods or logic as described herein. In a particular embodiment or aspect, the instructions 1220 may reside completely, or at least partially, within the main memory 1204, the static memory 1206, and/or within the processor 1202 during execution by the computing system 1200. The main memory 1204 and the processor 1202 also may include computer-readable media.

In an alternative embodiment or aspect, dedicated hardware implementations, such as application specific integrated circuits, programmable logic arrays and other hardware devices, can be constructed to implement one or more of the methods described herein. Applications that may include the apparatus and systems of various embodiments or aspects can broadly include a variety of electronic and computing systems. One or more embodiments or aspects described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments or aspects, the methods described herein may be implemented by software programs tangibly embodied in a processor-readable medium and may be executed by a processor. Further, in an exemplary, non-limited embodiment or aspect, implementations can include distributed processing, component/object distributed processing, and parallel processing. Alternatively, virtual computing system processing can be constructed to implement one or more of the methods or functionality as described herein.

It is also contemplated that a computer-readable medium includes instructions 1220 or receives and executes instructions 1220 responsive to a propagated signal, so that a device connected to a network 1224 can communicate voice, video or data over the network 1224. Further, the instructions 1220 may be transmitted or received over the network 1224 via the network interface device 1208.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any tangible medium that is capable of storing or encoding a set of instructions for execution by a processor or that cause a computing system to perform any one or more of the methods or operations disclosed herein.

In a particular non-limiting, example embodiment or aspect, the computer-readable medium can include a solid-state memory, such as a memory card or other package, which houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture and store carrier wave signals, such as a signal communicated over a transmission medium. A digital file attachment to an e-mail or other self-contained information archive or set of archives may be considered a distribution medium that is equivalent to a tangible storage medium. Accordingly, any one or more of a computer-readable medium or a distribution medium and other equivalents and successor media, in which data or instructions may be stored, are included herein.

In accordance with various embodiments or aspects, the methods described herein may be implemented as one or more software programs running on a computer processor. Dedicated hardware implementations including, but not limited to, application specific integrated circuits, programmable logic arrays, and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that software that implements the disclosed methods may optionally be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. The software may also utilize a signal containing computer instructions. A digital file attachment to e-mail or other self-contained information archive or set of archives is considered a distribution medium equivalent to a tangible storage medium. Accordingly, a tangible storage medium or distribution medium as listed herein, and other equivalents and successor media, in which the software implementations herein may be stored, are included herein.

Thus, a system and method to define a rotational source associated with a biological rhythm disorder, such a heart rhythm disorder, has been described herein. Although specific example embodiments or aspects have been described, it will be evident that various modifications and changes may be made to these embodiments or aspects without departing from the broader scope of the invention. Accordingly, the specification and drawings are to be regarded in an illustrative rather than a restrictive sense. The accompanying drawings that form a part hereof, show by way of illustration, and not of limitation, specific embodiments or aspects in which the subject matter may be practiced. The embodiments or aspects illustrated are described in sufficient detail to enable those skilled in the art to practice the teachings disclosed herein. Other embodiments or aspects may be utilized and derived therefrom, such that structural and logical substitutions and changes may be made without departing from the scope of this disclosure. This Detailed Description, therefore, is not to be taken in a limiting sense, and the scope of various embodiments or aspects is defined only by the appended claims, along with the full range of equivalents to which such claims are entitled.

Such embodiments or aspects of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments or aspects have been illustrated and described herein, it should be appreciated that any arrangement calculated to achieve the same purpose may be substituted for the specific embodiments or aspects shown. This disclosure is intended to cover any and all adaptations or variations of various embodiments or aspects. Combinations of the above embodiments or aspects, and other embodiments or aspects not specifically described herein, will be apparent to those of skill in the art upon reviewing the above description.

The Abstract is provided to comply with 37 C.F.R. § 1.72(b) and will allow the reader to quickly ascertain the nature and gist of the technical disclosure. It is submitted with the understanding that it will not be used to interpret or limit the scope or meaning of the claims.

In the foregoing description of the embodiments or aspects, various features are grouped together in a single embodiment for the purpose of streamlining the disclosure. This method of disclosure is not to be interpreted as reflecting that the claimed embodiments or aspects have more features than are expressly recited in each claim. Rather, as the following claims reflect, inventive subject matter lies in less than all features of a single disclosed embodiment or aspect. Thus the following claims are hereby incorporated into the Detailed Description, with each claim standing on its own as a separate example embodiment or aspect. It is contemplated that various embodiments or aspects described herein can be combined or grouped in different combinations that are not expressly noted in the Detailed Description. Moreover, it is further contemplated that claims covering such different combinations can similarly stand on their own as separate example embodiments or aspects, which can be incorporated into the Detailed Description.

The invention claimed is:

1. A method of defining a rotational source associated with a heart rhythm disorder, the method comprising:
   accessing, by a computing device, reconstructed signal data of heart signals, the reconstructed signal data having activation onset times associated with voltages at a plurality of time points;
   transforming, by the computing device, the reconstructed signal data from spline-sensor references to x-y coordinate locations;
   calculating, by the computing device, a plurality of center locations of wave fronts using the reconstructed signal data as transformed, at the plurality of time points associated with the rotational source, the wave fronts associated with the heart signals;
   determining, by the computing device, a rotational path that connects the plurality of center locations; and
   generating, by the computing device, a clinical representation that identifies a region of heart tissue associated with the rotational path.

2. The method of claim 1, wherein the method further comprises determining each of the wave fronts to include adjacent locations having at least a threshold voltage level surrounded by locations below the threshold voltage level.

3. The method of claim 2, wherein the threshold voltage level is a predetermined percentage of a highest voltage.

4. The method of claim 1, wherein the method further comprises determining a likely core associated with the rotational path.

5. The method of claim 4, wherein determination of the likely core associated with the rotational path comprises:
   calculating a plurality of relative diffusion shapes associated with the plurality of the center locations;
   determining a plurality of intersecting points of a smallest relative diffusion shape and other relative diffusion shapes within the rotational path; and
   defining a bounded polygon of the intersecting points as the likely core.

6. The method of claim 5, wherein calculation of a relative diffusion shape comprises:
   determining distances from locations in the wave front to a center location of the wave front; and
   calculating a circle having a radius equal to a predetermined multiplier multiplied by a standard deviation of the distances.

7. The method of claim 4, wherein determination of the likely core associated with the rotational path comprises:
   determining a convex hull around the rotational path;
   calculating a plurality of relative diffusion shapes associated with the plurality of the center locations;
   determining a plurality of intersecting points of a smallest relative diffusion shape and other relative diffusion shapes inside the convex hull; and
   defining a bounded polygon of the intersecting points as the likely core.

8. The method of claim 1, wherein calculation of a center location of a wave front comprises:
   averaging all first coordinates of locations associated with the wave front to generate a first average coordinate;
   averaging all second coordinates of the locations associated with the wave front to generate a second average coordinate; and
   defining the center location of the wave front as a location identified by the first average coordinate and the second average coordinate.

9. A system to define a rotational source associated with a heart rhythm disorder, the system comprising:
   a computing device; and
   a machine-readable medium to store instructions that, when executed by the computing device, cause the computing device to perform operations comprising:
      accessing reconstructed signal data of heart signals, the reconstructed signal data having activation onset times associated with voltages at a plurality of time points;
      transforming the reconstructed signal data from spline-sensor references to x-y coordinate locations;
      calculating a plurality of center locations of wave fronts using the reconstructed signal data as transformed, at the plurality of time points associated with the rotational source, the wave fronts associated with the heart signals;
      determining a rotational path that connects the plurality of center locations; and
      generating a clinical representation that identifies a region of heart tissue associated with the rotational path.

10. The system of claim 9, wherein the operations further comprise determining each of the wave fronts to include adjacent locations having at least a threshold voltage level surrounded by locations below the threshold voltage level.

11. The system of claim 10, wherein the threshold voltage level is a predetermined percentage of a highest voltage.

12. The system of claim 9, wherein the operations further comprise determining a likely core associated with the rotational path.

13. The system of claim 12, wherein operations for determination of the likely core associated with the rotational path further comprise:
   calculating a plurality of relative diffusion shapes associated with the plurality of the center locations;
   determining a plurality of intersecting points of a smallest relative diffusion shape and other relative diffusion shapes within the rotational path; and
   defining a bounded polygon of the intersecting points as the likely core.

14. The system of claim 13, wherein operations for calculation of a relative diffusion shape further comprise:
   determining distances from locations in the wave front to a center location of the wave front; and
   calculating a circle having a radius equal to a predetermined multiplier multiplied by a standard deviation of the distances.

15. The system of claim 12, wherein operations for determination of the likely core associated with the rotational path further comprise:
   determining a convex hull around the rotational path;
   calculating a plurality of relative diffusion shapes associated with the plurality of the center locations;
   determining a plurality of intersecting points of a smallest relative diffusion shape and other relative diffusion shapes inside the convex hull; and
   defining a bounded polygon of the intersecting points as the likely core.

16. The system of claim 9, wherein operations for calculation of a center location of a wave front further comprise:
   averaging all first coordinates of locations associated with the wave front to generate a first average coordinate;
   averaging all second coordinates of the locations associated with the wave front to generate a second average coordinate; and
   defining the center location of the wave front as a location identified by the first average coordinate and the second average coordinate.

17. A tangible computer-readable medium storing instructions that, when executed by a processor, cause the processor to perform operations for defining a rotational source associated with a heart rhythm disorder, the operations comprising:

accessing reconstructed signal data of heart signals, the reconstructed signal data having activation onset times associated with voltages at a plurality of time points;

transforming the reconstructed signal data from spline-sensor references to x-y coordinate locations;

calculating a plurality of center locations of wave fronts using the reconstructed signal data as transformed, at the plurality of time points associated with the rotational source, the wave fronts associated with the heart signals;

determining a rotational path that connects the plurality of center locations; and generating a clinical representation that identifies a region of heart tissue associated with the rotational path.

18. The tangible computer-readable medium of claim 17, wherein the operations further comprise determining each of the wave fronts to include adjacent locations having at least a threshold voltage level surrounded by locations below the threshold voltage level.

19. The tangible computer-readable medium of claim 18, wherein the threshold voltage level is a predetermined percentage of a highest voltage.

20. The tangible computer-readable medium of claim 17, wherein the operations further comprise determining a likely core associated with the rotational path.

21. The tangible computer-readable medium of claim 20, wherein operations for determination of the likely core associated with the rotational path further comprise:

calculating a plurality of relative diffusion shapes associated with the plurality of the center locations;

determining a plurality of intersecting points of a smallest relative diffusion shape and other relative diffusion shapes within the rotational path; and defining a bounded polygon of the intersecting points as the likely core.

22. The tangible computer-readable medium of claim 21, wherein operations for calculation of a relative diffusion shape further comprise:

determining distances from locations in the wave front to a center location of the wave front; and calculating a circle having a radius equal to a predetermined multiplier multiplied by a standard deviation of the distances.

23. The tangible computer-readable medium of claim 20, wherein operations for determination of the likely core associated with the rotational path further comprise:

determining a convex hull around the rotational path;

calculating a plurality of relative diffusion shapes associated with the plurality of the center locations;

determining a plurality of intersecting points of a smallest relative diffusion shape and other relative diffusion shapes inside the convex hull; and defining a bounded polygon of the intersecting points as the likely core.

24. The tangible computer-readable medium of claim 17, wherein operations for calculation of a center location of a wave front further comprise:

averaging all first coordinates of locations associated with the wave front to generate a first average coordinate;

averaging all second coordinates of the locations associated with the wave front to generate a second average coordinate; and defining the center location of the wave front as a location identified by the first average coordinate and the second average coordinate.

* * * * *